(12) United States Patent
Darcey

(10) Patent No.: US 6,835,182 B2
(45) Date of Patent: Dec. 28, 2004

(54) CUSTOM-MOLDABLE WRIST SPLINT

(75) Inventor: Thomas D. Darcey, Mooresville, NC (US)

(73) Assignee: BSN Medical, Inc., Wilmington, DE (US)

( * ) Notice: Subject to any disclaimer, the term of this patent is extended or adjusted under 35 U.S.C. 154(b) by 68 days.

(21) Appl. No.: 10/379,934

(22) Filed: Mar. 5, 2003

(65) Prior Publication Data

US 2004/0176714 A1 Sep. 9, 2004

(51) Int. Cl.$^7$ .................................................. A61F 5/00
(52) U.S. Cl. ........................ 602/20; 602/21; 128/878; 128/879
(58) Field of Search .................. 128/878, 879, 128/882; 602/4, 5, 6–10, 20, 21, 22

(56) References Cited

U.S. PATENT DOCUMENTS

| | | |
|---|---|---|
| 3,769,970 A | 11/1973 | Swanson |
| 4,524,464 A | 6/1985 | Primiano |
| 4,683,877 A | 8/1987 | Ersfeld |
| 4,716,892 A | 1/1988 | Brunswick |
| 4,770,299 A | 9/1988 | Parker |
| 4,852,557 A | 8/1989 | Grim |
| 4,928,678 A | 5/1990 | Grim |
| 4,941,460 A | 7/1990 | Working |
| 4,996,979 A | 3/1991 | Grim |
| 5,003,970 A | 4/1991 | Parker |
| 5,014,689 A | 5/1991 | Meunchen |
| 5,171,208 A | 12/1992 | Edenbaum |
| 5,318,504 A | 6/1994 | Edenbaum |
| 5,415,624 A | 5/1995 | Williams |
| 5,513,657 A | 5/1996 | Nelson |
| 5,520,621 A | 5/1996 | Edenbaum |
| 5,713,837 A | 2/1998 | Grim |
| 5,728,059 A * | 3/1998 | Wiesemann ................... 602/64 |
| 5,772,620 A | 6/1998 | Szlema |
| 5,787,896 A | 8/1998 | Sackett |
| 6,102,880 A | 8/2000 | Nelson |
| 6,106,492 A | 8/2000 | Darcey |
| 6,146,348 A | 11/2000 | Slautterback |
| 6,196,985 B1 | 3/2001 | Slautterback |
| 6,261,252 B1 | 7/2001 | Darcey |

FOREIGN PATENT DOCUMENTS

| | | |
|---|---|---|
| EP | 0 061 642 | 6/1982 |
| EP | 0 916 325 A1 | 5/1999 |
| FR | 486.552 | 1/1918 |

* cited by examiner

Primary Examiner—Michael A. Brown
(74) Attorney, Agent, or Firm—Adams Evans P.A.

(57) ABSTRACT

A wrist splint assembly for being custom-fitted to a hand and wrist to be supported. The wrist splint assembly includes a first splint for being positioned against and formed to the volar aspect of the hand and wrist, and a second splint for being positioned against and formed to the dorsal aspect of the hand and wrist. Each of the first and second splints defines a concave side edge extending inwardly toward the longitudinal axis of the splint for permitting ease of movement of the thumb and associated carpometacarpal joint of the hand against which the splint is positioned. Each splint also includes an inner cushion layer, an initially flexible intermediate layer overlying the inner cushion layer, and a flexible outer layer. The intermediate layer is a substrate impregnated with a moisture-curable resin that hardens upon curing to form a rigid structure of the substrate that retains a shape into which it is molded during curing for maintaining the flexible inner cushion layer in a conforming shape against the hand and wrist. A support retains the first and second splints in position on the hand and wrist during use of the splint assembly.

17 Claims, 14 Drawing Sheets

CUSTOM-MOLDABLE WRIST SPLINT

TECHNICAL FIELD AND BACKGROUND OF THE INVENTION

This invention relates generally to the field of orthopedic medicine and more specifically to a custom-moldable wrist splint and a method for using such a splint to relieve and treat the symptoms of carpal tunnel syndrome.

Carpal tunnel syndrome occurs as a result of chronic irritation to the median nerve. The median nerve and the tendons that connect the muscles of the forearm to the fingers of the hand pass through the carpal tunnel. The carpal tunnel is a passageway defined by the eight carpal bones of the wrist and the transverse carpal ligament, which interconnects the hook of the hamate and the tubercle of the trapezium. Carpal tunnel syndrome results when the median nerve becomes constricted within the carpal tunnel, usually by the swelling of the tendons. Such constriction pushes the median nerve against the transverse carpal ligament located directly above the nerve.

The median nerve relays sensation from the palm of the hand and fingers. Continuous constriction of the median nerve causes it to gradually deteriorate, which in turn causes numbness, tingling and pain in the fingers and hand. Occasionally, such constriction also produces pain and parasthesia in the arm and shoulder. If left untreated, carpal tunnel syndrome can ultimately cause the muscles on the affected hand to weaken and atrophy.

Causes of carpal tunnel syndrome are controversial. However, the syndrome has been attributed to those repetitive uses of the hand and wrist that require forceful movements in which the wrist is extended. Such uses include, but are not limited to, using a keyboard or a screwdriver. Pregnant women and persons with diabetes or hypothyroidism are at an increased risk of developing carpal tunnel syndrome.

Severe cases of carpal tunnel syndrome are often treated by injecting corticosteroids into the affected nerve. The syndrome is also treated using a surgical procedure known as a "carpal tunnel release" in which the bands of tendons placing pressure on the median nerve are released. Although severe cases of carpal tunnel syndrome may require pharmaceutical or surgical intervention, the vast majority of cases may be resolved using much simpler methods, especially when treatment is initiated at the onset of symptoms. One form of early treatment is to splint the hand and wrist to provide support to the muscles of the hand and wrist. This treatment, combined with rest and correction or elimination of the suspected environmental factors contributing to the symptoms (for example, repositioning or changing a computer keyboard), can often avoid the need for injections or surgery.

Prior art splints often include a soft component to place near the skin and a hard, shell-like outer cover. The soft component is intended not only to cushion against the injured anatomy, but also to accommodate itself to the varying configurations of differing sized and shaped anatomy of patients. Other splints are glove-like in design and are provided with bendable plastic or metal stays that are bent to maintain the hand and wrist in a desired position.

Some prior art splints are constructed of or include thermosetting materials. Such materials are first heated and then formed to the hand and wrist while the materials are still warm. Splints formed from thermosetting materials cannot be used without a heat source, and the splints are susceptible to over-or-underheating. In addition, body heat can soften or at least increase the flexibility of the splint, which decreases the effectiveness of the protection offered by the splint.

The present invention overcomes the disadvantages of prior art splints by providing a splint that can be applied to the hand and wrist in such a way as to achieve a true custom fit from a universal design. The invention utilizes a moisture-curable resin which results in a very rigid splint that holds the shape into which it has been molded. No heat is required. A source of water is the only additional material necessary to harden the splint. Atmospheric moisture alone will cure the splint into its hardened position in a relatively short period of time; however, the resin in or on the splint will typically be activated by immersing the splint in water.

The splint is inexpensive, easy to fabricate, easy to fit and comfortable to wear. Since the splint has a single shape and size, hospitals, clinics, emergency care facilities and other health care providers can easily and inexpensively maintain a necessary inventory of splints.

In contrast to those prior art splints which are applied only to the dorsal aspect of the wrist, the splints of the present invention are utilized in pairs. Two of the splints are custom-fitted to the affected hand and wrist—one on the dorsal aspect and one on the volar aspect thereof—to achieve a true four-point fixation of the injury. Unlike other splints which are utilized in pairs, the splints of the present invention feature a unique shape that accommodates and enables movement of the thumb and associated carpometacarpal joint while simultaneously providing enhanced support to the heads of the second through fourth metacarpals and metacarpophalangeal joints associated therewith. This provides greater support to the injured area and reduces the extent of residual movement of the hand and wrist.

SUMMARY OF THE INVENTION

Therefore, it is an object of the invention to provide a wrist splint assembly having two splints that are interchangeable between left and right hands.

It is another object of the invention to provide a wrist splint assembly that can be easily placed on and removed from the hand and wrist by the patient.

It is another object of the invention to provide a wrist splint assembly including a wrist splint that is interchangeable between the volar aspect of one hand to the dorsal aspect of the other hand prior to being hardened into a custom-fitted shape.

It is another object of the invention to provide a wrist splint assembly that allows enhanced mobility of the thumb and associated carpometacarpal joint while simultaneously providing increased support of the heads of the second through fourth metacarpals and carpometaphalangeal joints associated therewith.

It is another object of the invention to provide a wrist splint that is stored in a secondary, cure-retarding inner package, which is in turn sealed within an outer moisture-proof pouch, until the splint is ready for being applied to the body part to be protected.

It is another object of the invention to provide a wrist splint assembly that includes two or more splints sealed within a single moisture-impervious package for ease of removal and use.

It is another object of the invention to provide a wrist splint that hardens in the presence of moisture to form a very lightweight, protective splint.

These and other objects of the present invention are achieved in the preferred embodiments disclosed below by providing a wrist splint assembly for being custom-fitted to a hand and wrist to be supported. The wrist splint assembly includes a first splint for being positioned against and formed to the volar aspect of the hand and wrist, and a second splint for being positioned against and formed to the dorsal aspect of the hand and wrist. Each of the first and second splints defines a concave side edge extending inwardly toward the longitudinal axis of the splint for permitting ease of movement of the thumb and associated carpometacarpal joint of the hand against which the splint is positioned. Each of the first and second splints also includes an inner cushion layer for being placed on and conformed to the shape of the hand and wrist, and an initially flexible intermediate layer overlying the inner cushion. The intermediate layer is a substrate impregnated with a moisture-curable resin that hardens upon curing to form a rigid structure of the substrate that retains a shape into which it is molded during curing for maintaining the flexible inner cushion layer in a conforming shape against the hand and wrist. Each of the first and second splints also includes a flexible outer layer overlying the intermediate layer and attached to the inner cushion layer for enclosing the intermediate layer for forming the inner layer, intermediate layer and outer layer into a single, integrated splint structure. The wrist splint assembly also includes a support for retaining the first and second splints in position on the hand and wrist during use of the splint assembly.

According to one preferred embodiment of the invention, the support is an elongate strap having an outer surface and first and second ends. The first end of the strap is releasably attached to a complementary fastener attached to a preselected one of the outer layers of the first and second splints. The second end of the strap is releasably attached to the outer surface of the strap, thereby permitting the strap to encircle the wrist for securing the first and second splints against the hand and wrist.

According to another preferred embodiment of the invention, the support also includes a second elongate strap having an outer surface and first and second ends. The first end of the second strap is releasably attached to a complementary second fastener attached to a preselected one of the outer layers of the first and second splints. The second end of the second strap is releasably attached to the outer surface of the second strap, thereby permitting the second strap to encircle the wrist for securing the first and second splints against the hand and wrist.

According to yet another preferred embodiment of the invention, the support also a third elongate strap having an outer surface and first and second ends. The first end of the third strap is releasably attached to a complementary third fastener attached to a preselected one of the outer layers of the first and second splints. The second end of the third strap is releasably attached to the outer surface of the third strap, thereby permitting the third strap to encircle the hand for securing the first and second splints against the hand and wrist.

According to yet another preferred embodiment of the invention, the fastener, second fastener, and third fastener are patches of hooked material.

According to yet another preferred embodiment of the invention, the outer surface of the strap, second strap and third strap are formed from looped material.

According to yet another preferred embodiment of the invention, the support includes a plurality of elongate straps releasably attached to a plurality of complementary fasteners attached to the outer layer of the splint for permitting the straps to encircle and hold the splint in place against the wearer's hand and wrist while being worn.

According to yet another preferred embodiment of the invention, each of the straps includes a patch of looped material attached to an end of the strap for cooperating with a complementary outer surface of the strap for holding the first and second splints in place against the hand and wrist while being worn.

According to yet another preferred embodiment of the invention, the wrist splint assembly includes a moisture-proof pouch in which the first and second splints are maintained in a flexible condition in a moisture-free environment until the pouch is opened immediately prior to applying one of the splints to the hand and wrist.

According to yet another preferred embodiment of the invention, the outer moisture-proof pouch is formed of a laminated structure having at least one layer of plastic film and at least one layer of aluminum foil bonded to the plastic film.

According to yet another preferred embodiment of the invention, the substrate includes a plurality of overlaid thicknesses of fiberglass.

According to yet another preferred embodiment of the invention, the plurality of thicknesses of fiberglass includes at least five thicknesses and no more than seven thicknesses.

According to yet another preferred embodiment of the invention, a wrist splint product is provided for being custom-fitted to a hand and wrist to be supported. The wrist splint product includes first and second splints. Each of the first and second splints defines a concave side edge extending inwardly toward the longitudinal axis of the splint for permitting enhanced movement of the thumb and associated carpometacarpal joint of the hand. Each splint is formed of a fabric impregnated with a moisture-curable resin that hardens upon curing to form a rigid structure of the fabric that retains a defined shape into which the fabric is molded during curing. The splint product also includes first and second inner storage pouches constructed of a plastic film having moisture-transmission retarding properties, one of the first or second splints being sealed in respective ones of the first and second storage pouches, and a single, outer moisture-proof protective pouch within which the first and second splints and respective first and second inner storage pouches are sealed in the absence of moisture until the first and second splints are to be molded to the body part to be protected.

According to yet another preferred embodiment of the invention, the outer moisture-proof protective pouch is formed of a laminated structure having at least one layer of plastic film and at least one layer of aluminum foil bonded to the plastic film.

According to yet another preferred embodiment of the invention, the plastic film has a thickness of 2 mils and the aluminum foil layer has a thickness of 0.5 mils.

According to yet another preferred embodiment of the invention, the outer moisture-proof protective pouch includes a laminated layer of nylon film.

A preferred embodiment of a method of forming a custom-fitted wrist splint to a hand and wrist includes the steps of providing a first splint for being positioned against and formed to the volar aspect of the hand and wrist, and a second splint for being positioned against and formed to the dorsal aspect of the hand and wrist. Each of the first and second splints includes a multi-layered protective pad positioned in flexible condition in a moisture-impervious storage package and sealed therein against entry of moisture until use. Each of the first and second splints defines a concave side edge extending inwardly toward the longitudinal axis of the splint for permitting ease of movement of the thumb and associated carpometacarpal joint of the hand against which the splint is positioned, and includes an inner cushion layer for being placed on and conformed to the shape of the hand and wrist and an initially flexible intermediate layer overlying the inner cushion layer. The intermediate layer includes a substrate impregnated with a moisture-curable resin that hardens upon curing to form a rigid structure of the substrate that retains a shape into which it is molded during curing for maintaining the flexible inner cushion layer in a conforming shape against the hand and wrist. Each of the first and second splints also includes a flexible outer layer overlying the intermediate layer and attached to the inner cushion layer for enclosing the intermediate layer for forming the inner layer, intermediate layer and outer layer into a single, integrated splint structure. A support is carried by the first and second splints for retaining the first and second splints in position on the hand and wrist during use of said wrist splint. The method also includes the steps of removing a preselected one of the first and second splints from the storage package, exposing the splint to moisture in an amount sufficient to activate the moisture-curable resin, placing the splint against the hand and wrist, and exerting pressure on the splint for a sufficient period of time for the pad to harden, whereby the pad hardens into a rigid, supporting shape custom-fitted to the hand and wrist.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
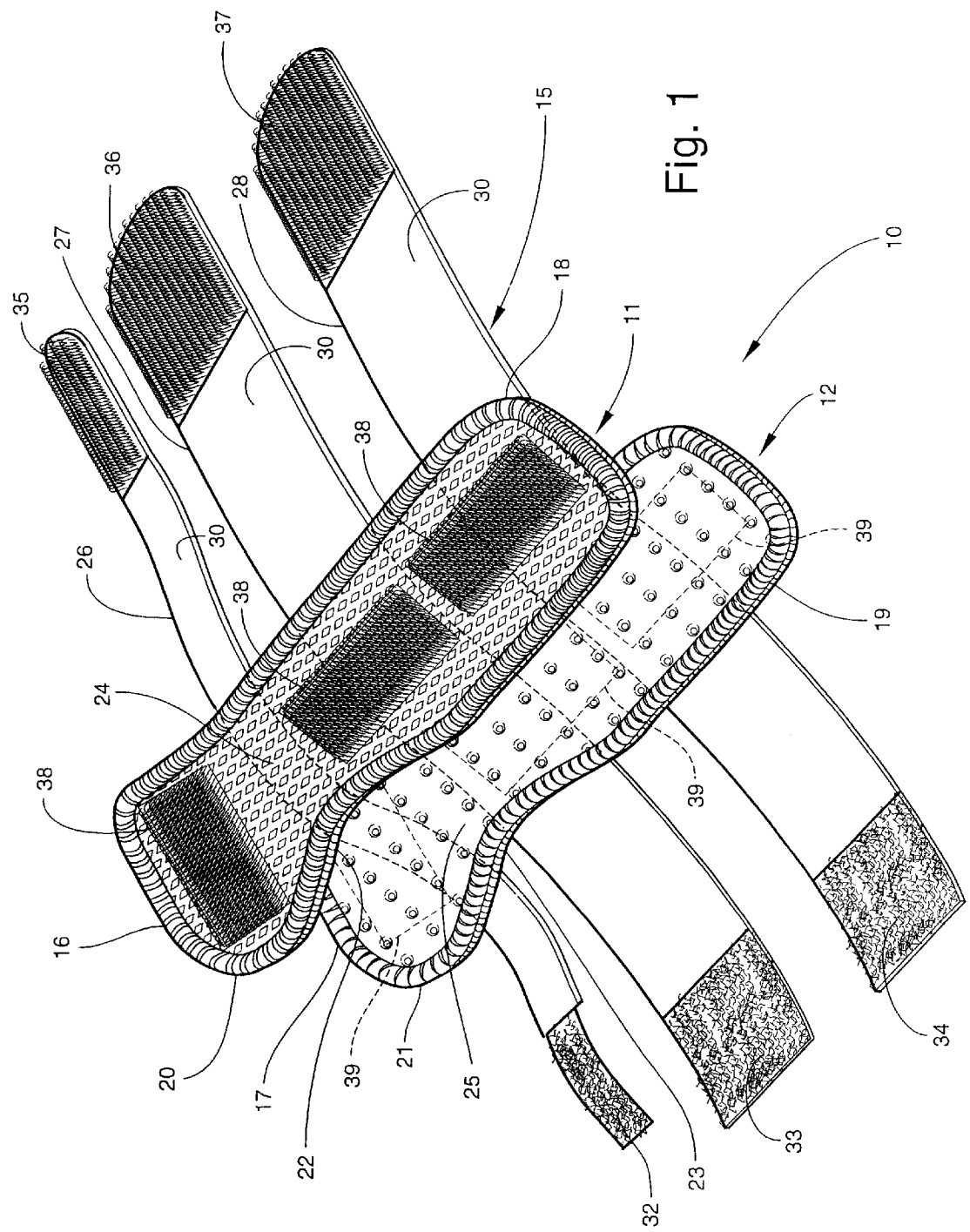
FIG. 1 is a perspective view of a wrist splint assembly according to a preferred embodiment of the invention.

Referring now specifically to the drawings, a wrist splint assembly according to one preferred embodiment of the invention is illustrated in FIG. 1 and shown generally at reference numeral 10. The splint assembly 10 includes two splints 11 and 12 which, as described more fully below with reference to FIGS. 10 through 13, are custom-molded to fit against the dorsal and volar aspects of the hand and wrist of a wearer. The splints 11 and 12 are held in place by a strap assembly 15.

Referring again to FIG. 1, the splints 11 and 12 include upper end portions 16 and 17, which are integrally formed with respective elongate lower end portions 18 and 19. The upper end portions 16 and 17 are wider than the lower end portions 18 and 19, and define rounded, convex side edges 20 and 21, respectively. As is shown in FIGS. 2 and 3, the increased width and rounded side edges 20 and 21 permit the respective upper end portions 16 and 17 to extend across and support the second through fourth metacarpals of a hand positioned between the splints 11 and 12.

Referring again to FIG. 1, the lower end portions 18 and 19 and upper end portions 16 and 17 of the splints 11 and 12 are interconnected by respective side edges 22 and 23. Side edges 22 and 23 are connected to and integrally formed with rounded side edges 20 and 21, respectively. The side edges 22 and 23 curve inwardly relative to the respective longitudinal axes of the splints 11 and 12 to define concave areas 24 and 25. As is shown in FIGS. 2 and 3, the concave areas 24 and 25 are positioned adjacent the respective upper end portions 16 and 17, and collectively define an open space within which the carpometacarpal joint ("CM") and associated anatomy of the wearer's thumb "T" may freely move.

Referring again to FIG. 1, the strap assembly 15 includes a narrow strap 26 and two wide straps 27 and 28. Each strap 26, 27 and 28 is preferably formed from a length of knitted or woven material having two surfaces formed from loose, fibrous coverings 30 and 31 (fibrous covering 31 is shown in FIG. 2). A patch of fibrous material 32, 33 and 34 is connected to one end of each strap 26, 27 and 28, respectively, and patches of hooked material 35, 36 and 37 are attached to the respective opposite ends of the straps 26, 27 and 28.

Figure 2:
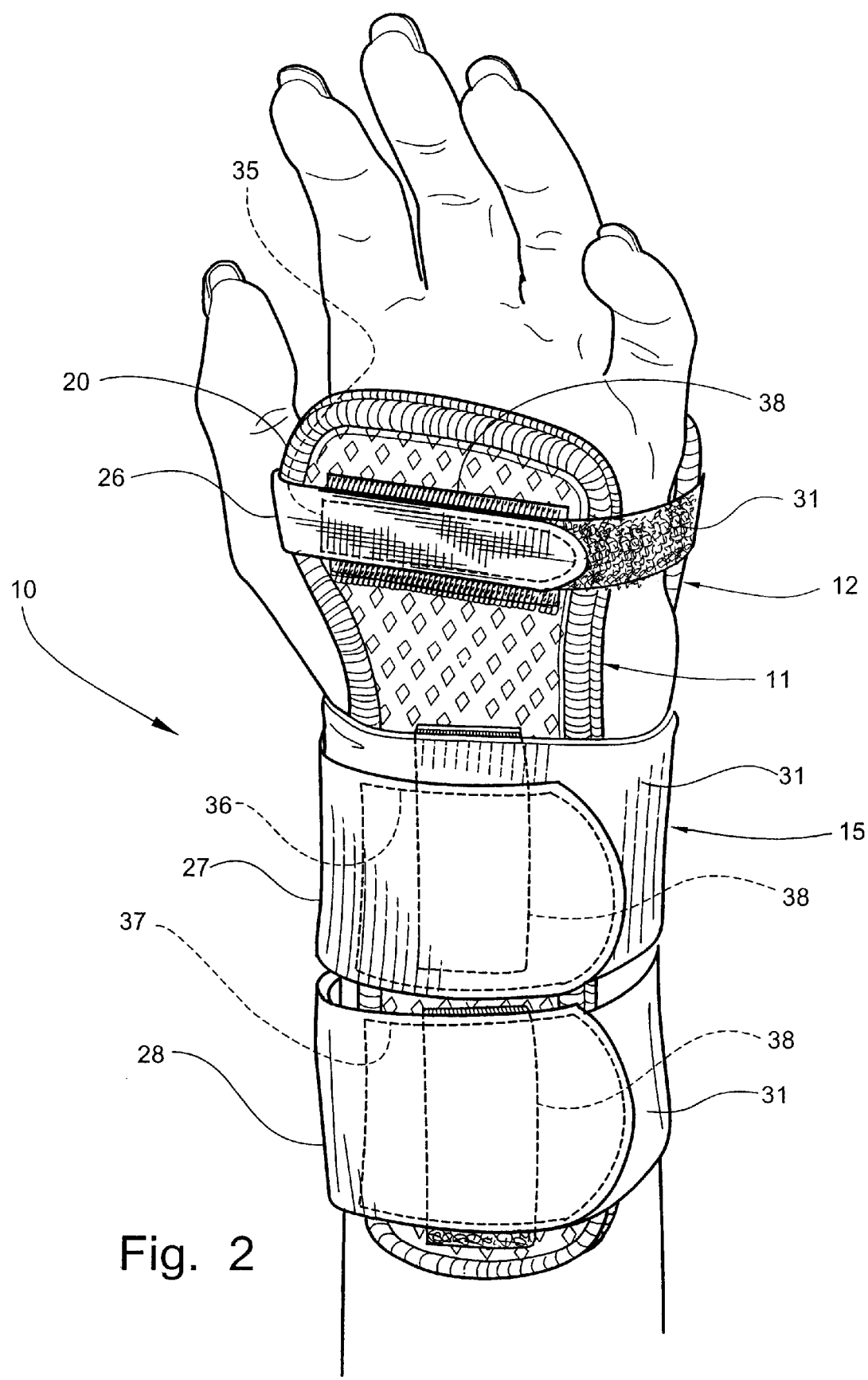
FIG. 2 is an environmental perspective view of the wrist splint assembly according to FIG. 1 secured to the left hand and wrist of a wearer.
Figure 3:
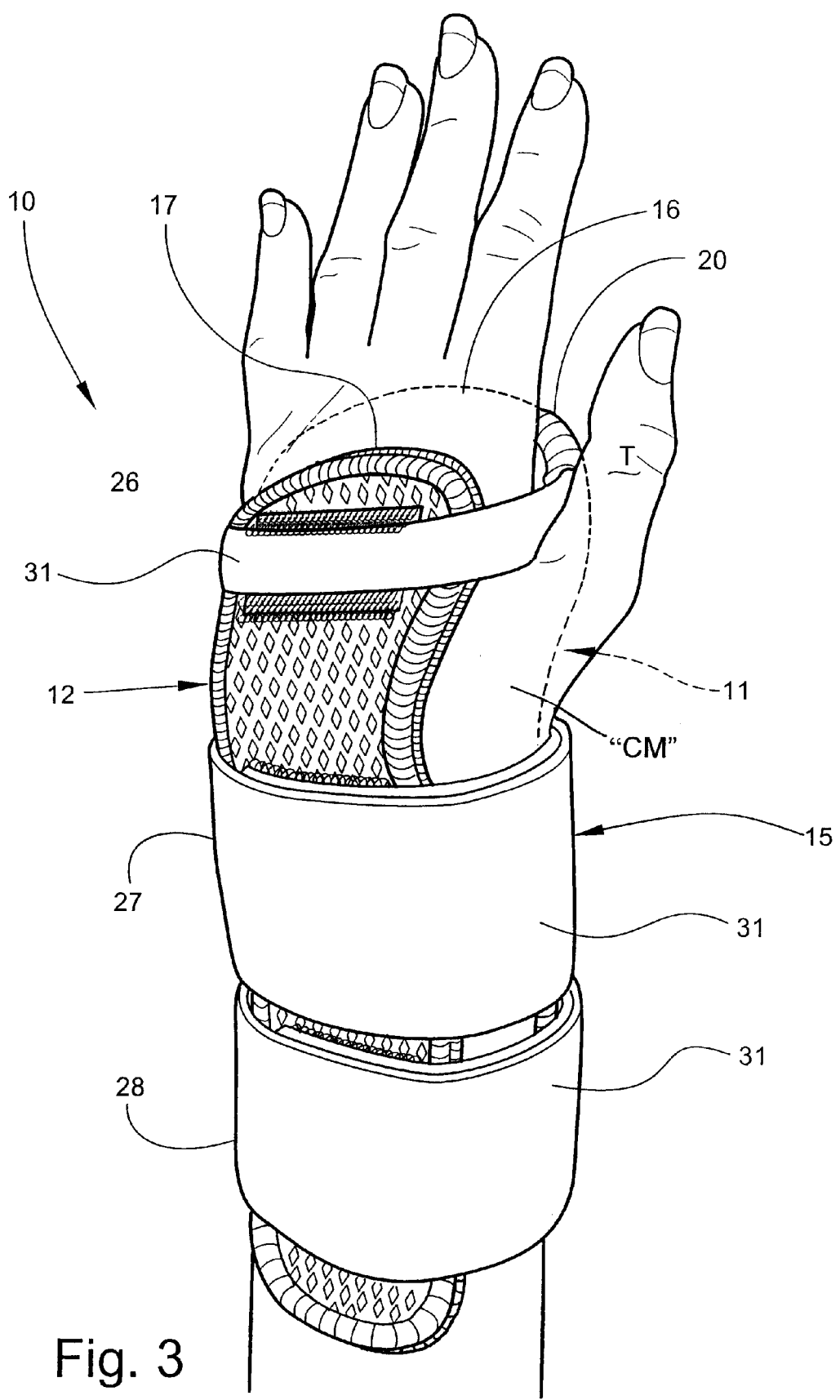
FIG. 3 is an environmental perspective view of the dorsal aspect of the wearer's left hand and wrist with the wrist splint assembly secured thereto.

Referring now to FIGS. 2 through 5, the manner in which the strap assembly 15 extends around the wrist and hand of the wearer to maintain the splints 11 and 12 against the hand is shown. As is shown in FIG. 2, the straps 26, 27 and 28 are used to hold the splints 11 and 12 in place against a wearer's hand and wrist by first releasably attaching each fibrous patch 32, 33 and 34 (see FIG. 1) to a respective one of three identically-shaped patches of hooked material 38 positioned on splint 12. As is shown in FIG. 3, each of the straps 26, 27 and 28 are wrapped around the wearer's forearm and over splint 11, which releasably attaches the fibrous covering 30 on each strap 26, 27 and 28 to a respective one of three identically-shaped patches of hooked material 39 positioned on splint 12 (see FIG. 1). Referring again to FIG. 2, the straps 26, 27 and 28 are wrapped around the wearer's forearm again, and the patches of hooked material 35, 36 and 37 are releasably attached to the fibrous covering 31 of the respective straps 25, 26 and 27. This positions the patches of hooked material 35, 36 and 37 in overlying relation to the fibrous patches 32, 33 and 34, respectively.

The straps 26, 27 and 28 may be wrapped in any suitable manner around the splints 11 and 12. However, the straps 26, 27 and 28 are preferably oriented around the splints 11 and 12 so that the strap 26 encircles the respective upper end portions 13 and 14 and straps 27 and 28 encircle the respective lower end portions 15 and 16. This ensures that a true four-point fixation of the injury is achieved and maintained.

Figure 4:
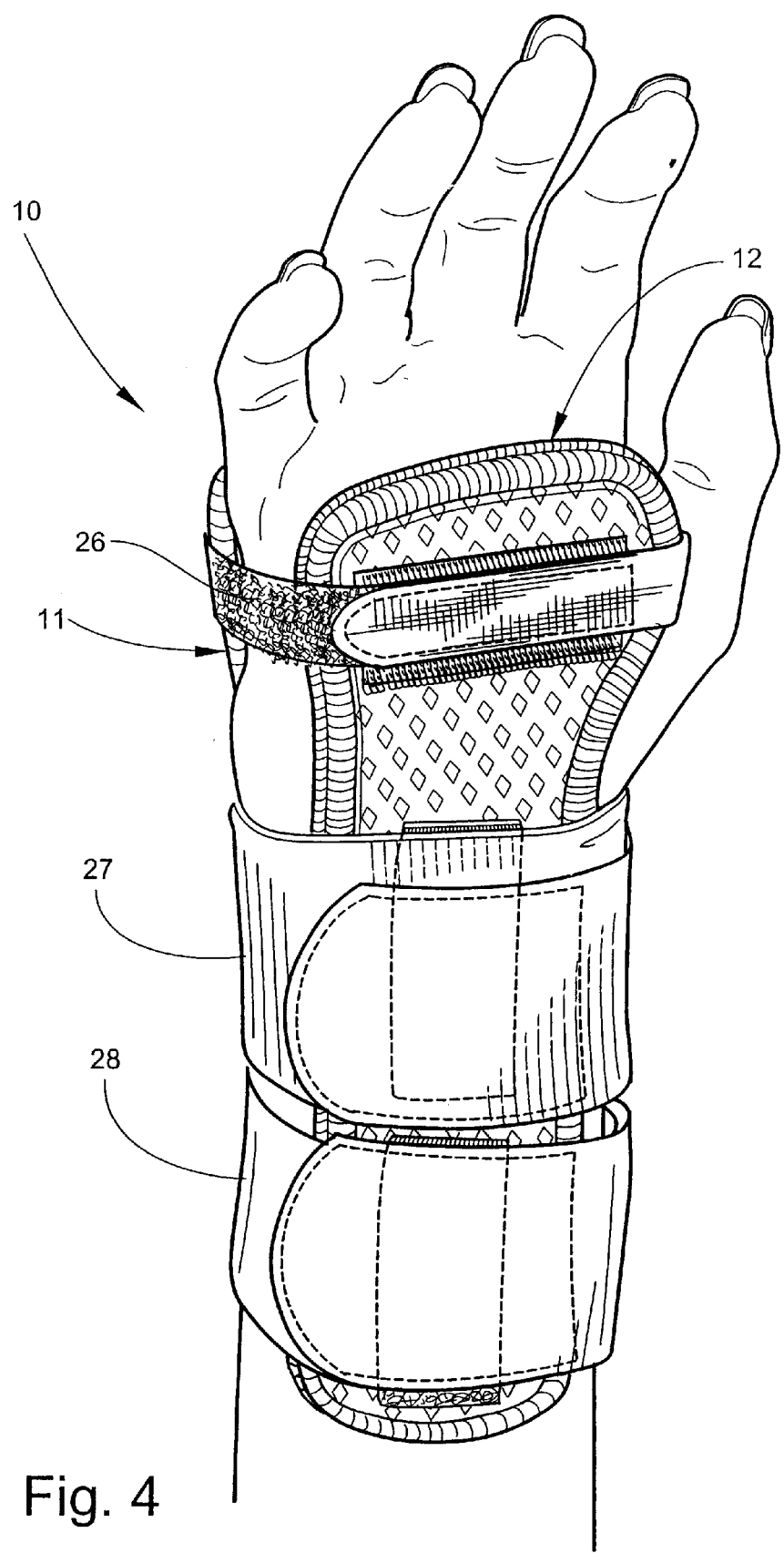
FIG. 4 is an environmental perspective view of the wrist splint assembly according to FIG. 1 secured to the volar aspect of the right hand and wrist of a wearer.

Although the splint assembly 10 is shown in FIGS. 2 and 3 being worn on the left hand with the splint 11 positioned against the volar aspect, and the splint 12 positioned against the dorsal aspect of the hand and wrist, the splints 11 and 12 may be interchanged and worn on the opposite hand. FIG. 4 shows the splint assembly 10 worn on the right hand, with splint 12 positioned on the volar aspect and splint 11 positioned on the dorsal aspect of the hand and wrist.

The splints 11 and 12 are chiral objects: they are mirror images of and cannot be superposed upon each other. This is due to the unique shape of the upper end portions 16 and 17 and concave areas 24 and 25 of the respective splints 11 and 12. As described in greater detail below with reference to FIG. 6, different materials are utilized on the opposing surfaces of each splint 11 and 12, which also contributes to their chirality and limits the number of positions in which the splints 11 and 12 may be positioned against the wrists and hands. Specifically, the splint 11 may be custom-molded to be worn on the volar aspect of the wearer's left hand (FIGS. 2 & 3) or the dorsal aspect of the wearer's right hand (FIG. 4). In contrast, the splint 12 may be custom-molded and worn on the dorsal aspect of the wearer's left hand (FIGS. 2 & 3) or the volar aspect of the wearer's right hand (FIG. 4).

Figure 5:
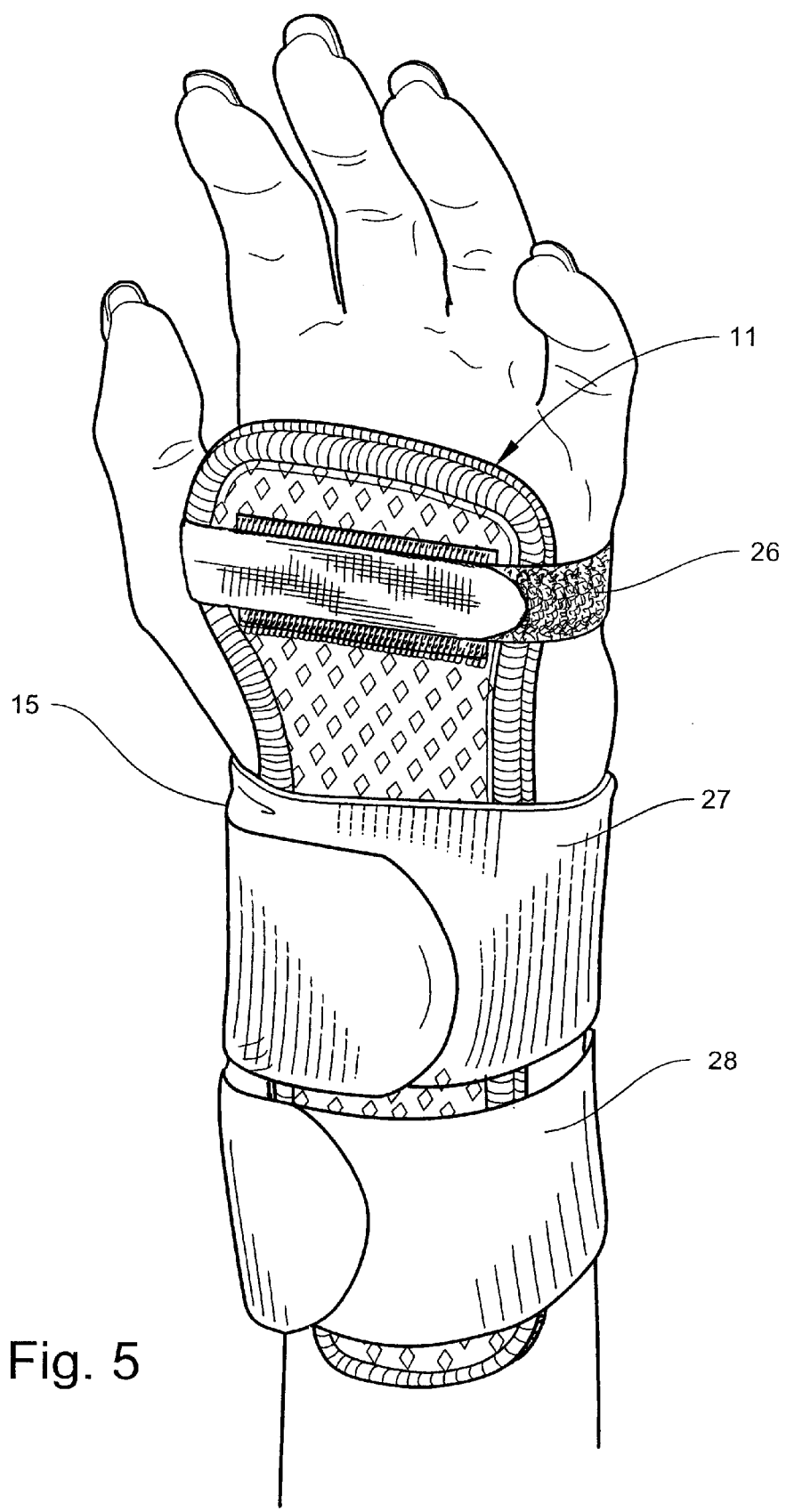
FIG. 5 is an environmental perspective view of a single wrist splint and support according to a preferred embodiment of the invention secured to the volar aspect of a wearer's left hand.

Although FIGS. 2 through 4 illustrate the splints 11 and 12 being worn simultaneously with the affected hand and wrist positioned therebetween, the splints 11 and 12 do not have to be worn in pairs. FIG. 5 shows a single splint 11 positioned against the volar aspect of a wearer's left hand and held in place by the strap assembly 15.

Figure 6:
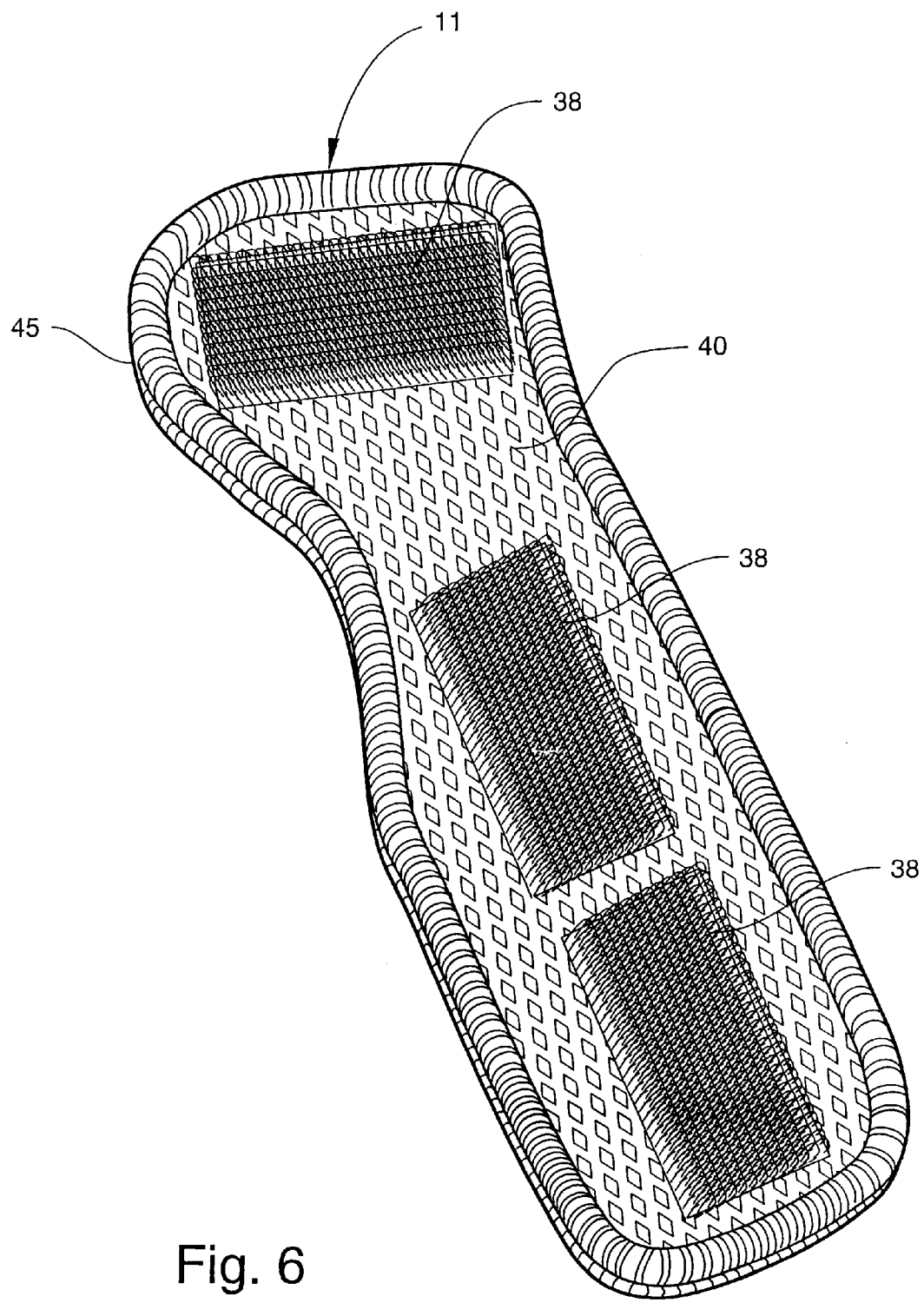
FIG. 6 is a perspective view of the outer side of a splint according to a preferred embodiment of the invention.
Figure 7:
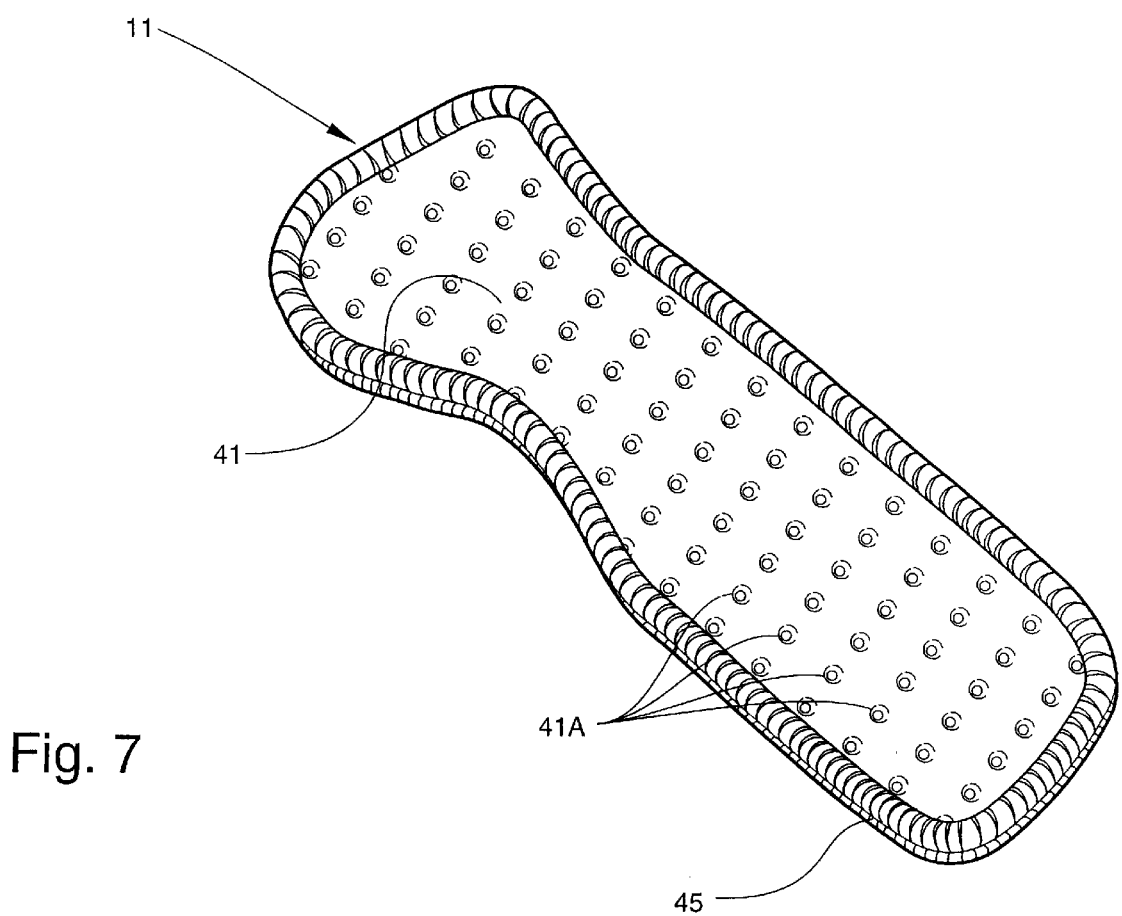
FIG. 7 is a perspective view of the inner side of a splint according to FIG. 6.
Figure 8:
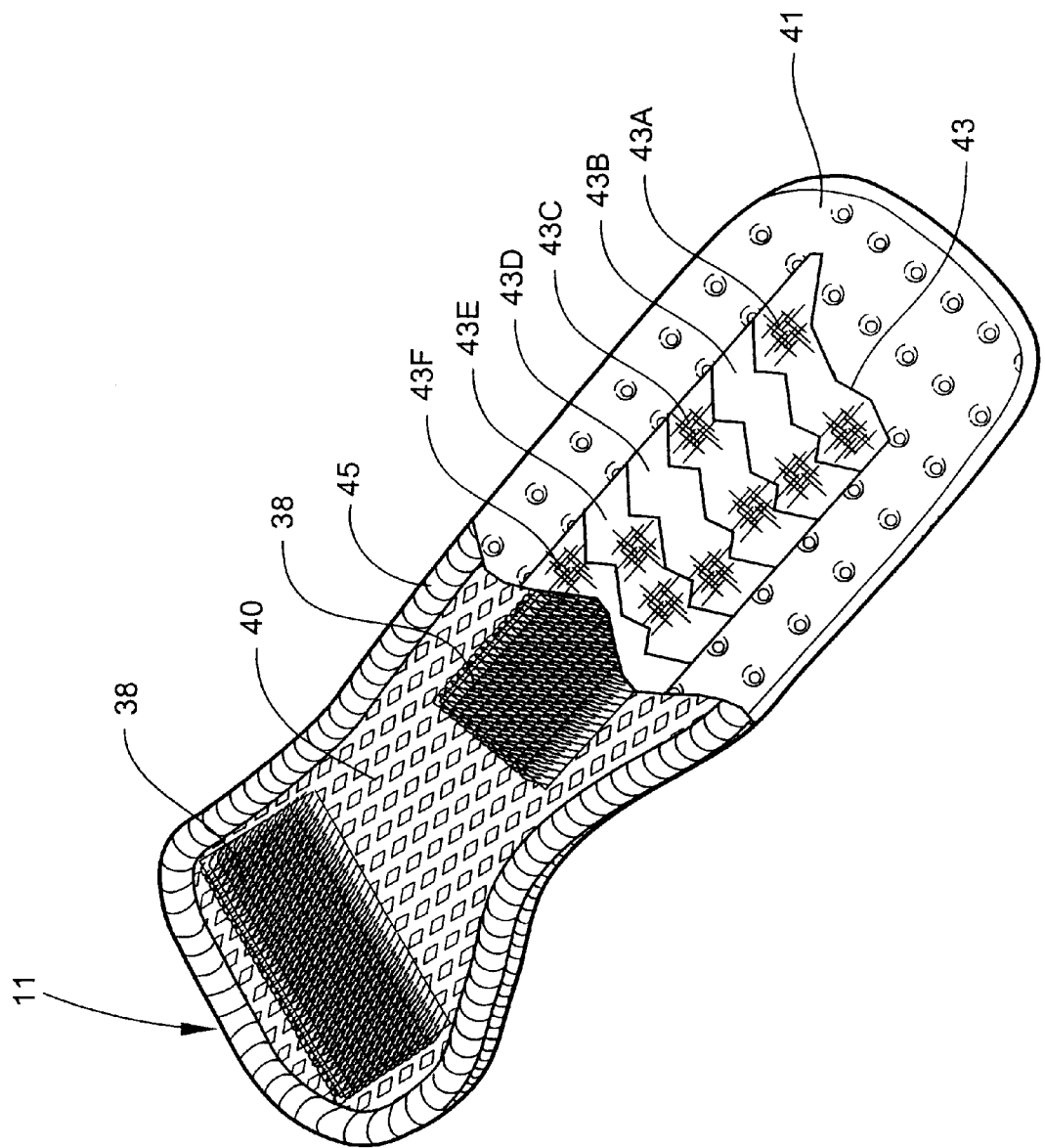
FIG. 8 is a perspective view of a splint according to FIG. 6, with parts broken away and with the intermediate layer exposed for clarity.

Referring now to FIGS. 6 through 8, the materials used to construct the splints 11 and 12 are shown. Using the splint 11 as a representative example, FIG. 6 shows the splint 11 prior to being custom-fitted against a wearer's hand. The splint 11 includes an outer layer 40 formed from a fabric casing to which the three patches of hook-and-loop material 38 are sewn. Although any suitable material may be used, the outer layer 40 is preferably formed from polyester sheeting.

Referring now to FIG. 7, the splint 11 also includes a flexible inner cushion layer 41. Inner cushion layer 41 is preferably a laminated one-eighth inch, four pound EVA (ethylene vinyl acetate) micro-perf closed cell foam. The EVA is flexible enough to bend easily with the other components of the splint 11. The inner cushion layer 41 is placed closest to the body member to be protected, and provides a comfortable surface next to the skin. As is shown in FIG. 7, the inner cushion layer 41 includes a plurality of spaced-apart ventilation holes 41A. The ventilation holes 41A allow water to quickly pass though the cushion layer 41 to rapidly penetrate the splint 11 during the curing process. The holes 41A also promote improved air flow and cooling of the splint 11 during wear.

Referring now to FIG. 8, the splint 11 also includes an initially flexible intermediate layer 43. Intermediate layer 43 is sandwiched between the outer layer 40 and the inner cushion layer 41. The intermediate layer 43 is preferably formed from fiberglass fabric layers 43A through 43F, each of which is impregnated with a moisture-curable resin that hardens upon curing to form a rigid structure that retains the shape of the hand and wrist onto which the splint 11 has been molded. Although any suitable number of fabric layers may be used, the intermediate layer 43 preferably includes three to seven fabric layers. The embodiment of the invention shown in FIGS. 6 through 8 includes six layers.

Other materials which may be suitable for forming the intermediate layer 43 include materials formed from a composition of aluminum oxide, silicone oxide and boron oxide and sold under the name NEXTEL 440 by Thermostatic Industries, Inc.

Each of the fiberglass fabric layers 43A through 43F are impregnated or coated with a moisture-curable resin such as the polyisocyanate resin which is described in full in U.S. Pat. No. 4,770,299. The resin is synthesized using a reactive system that remains stable when maintained in substantially moisture-free conditions, yet hardens upon exposure to sufficient moisture to form a rigid, self-supporting structure. A typical formulation of the reactive system is as follows:

Typical Formulation

| Isonate↓ 143L or Mondur↓ CD or Rubinate↓ XI168 | polyisocyanate | 50.0% |
|---|---|---|
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262.

The polyisocyanate resin remains in a viscous state as long as the resin is not exposed to moisture. This permits the intermediate layer 43 to remain flexible and moldable so long as the resin is not exposed to moisture, and for a short period of time after such exposure occurs. The rate at which the resin cures can be controlled to some extent by adjusting the quantity of water to which the resin is exposed. Briefly immersing the resin in water will cause the resin to rapidly cure. In contrast, merely exposing the resin to open air will result in a curing process having a significantly slower reaction rate that will be proportional to the amount of moisture in the air to which the resin has been exposed.

Alternate embodiments of the invention may employ an intermediate layer 43 formed from a single substrate layer, particularly if materials other than fiberglass are used. One preferred alternative material from which the intermediate layer 43 may be formed is a single ply sheet of random-laid noncontinuous polyester nonwoven fabric that incorporates a styrene-soluble binder filled with plastic microspheres to 60 percent by volume. Such a fabric is sold under the trademark FIRET COREMAT XM by Baltek. This fabric is available in 2 mm, 3 mm and 4 mm thicknesses. Other grades, such as the products sold under the trademarks FIRET COREMAT XX and FIRET COREMAT XW may also be used. These grades are filled with plastic microspheres to 50 percent by volume.

Other products which may be suitable for use include a low density, nonwoven continuous strand fabric such as that sold under the trademark BALTEKMAT T-2000. This product has characteristics which are generally similar to FIRET COREMAT products, but is generally not available in small quantities. As noted above, only a single thickness of any one of these alternative substrate materials may be necessary. Another alternative substrate material is a fabric woven or knitted from polypropylene yarns. Such fabric is somewhat more flexible than fiberglass fabric after hardening, and offers some cost savings during production of the splints 11 and 12.

In accordance with the invention, the individual fiberglass fabric layers 43A through 43F are preferably die-cut to shape. In addition, while each of the fabric layers 43A through 43F preferably have the same width, the layers 43A through 43F may alternatively have varying widths. The degree of overlap and non-overlap resulting from the differing widths provides a variable thickness across the intermediate layer 43 after curing, with a relatively thick predetermined area where increased rigidity is desired and a relatively thin area where increased flexibility is desired. The manner of varying the widths of the fabric layers 43A through 43F is described in detail in Applicant's prior U.S. Pat. No. 5,755,678.

Referring again to FIG. 8, the outer layer 40 and the inner cushion layer 41 are joined around the perimeter by a seam 45 to enclosed the intermediate layers 43A through 43F between the outer layer 40 and cushion layer 41. The outer layer 40 and cushion layer 41 are preferably sewn together using an overedge or serging seam. Although the outer layer 40 and cushion layer 41 have thermoplastic properties, the outer layer 40 and cushion layer 41 may alternatively be bonded together around the edge using radio-frequency ("RF") welding. RF welding is a particularly efficient method of bonding because it permits tight corners and curves to be formed in the splint 11, some of which are difficult to form using conventional sewing techniques. The intermediate cushion layer 43 may alternatively be enclosed between the outer layer 40 and the cushion layer 41 using ultrasonic sealing or other suitable adhesives.

Figure 9:
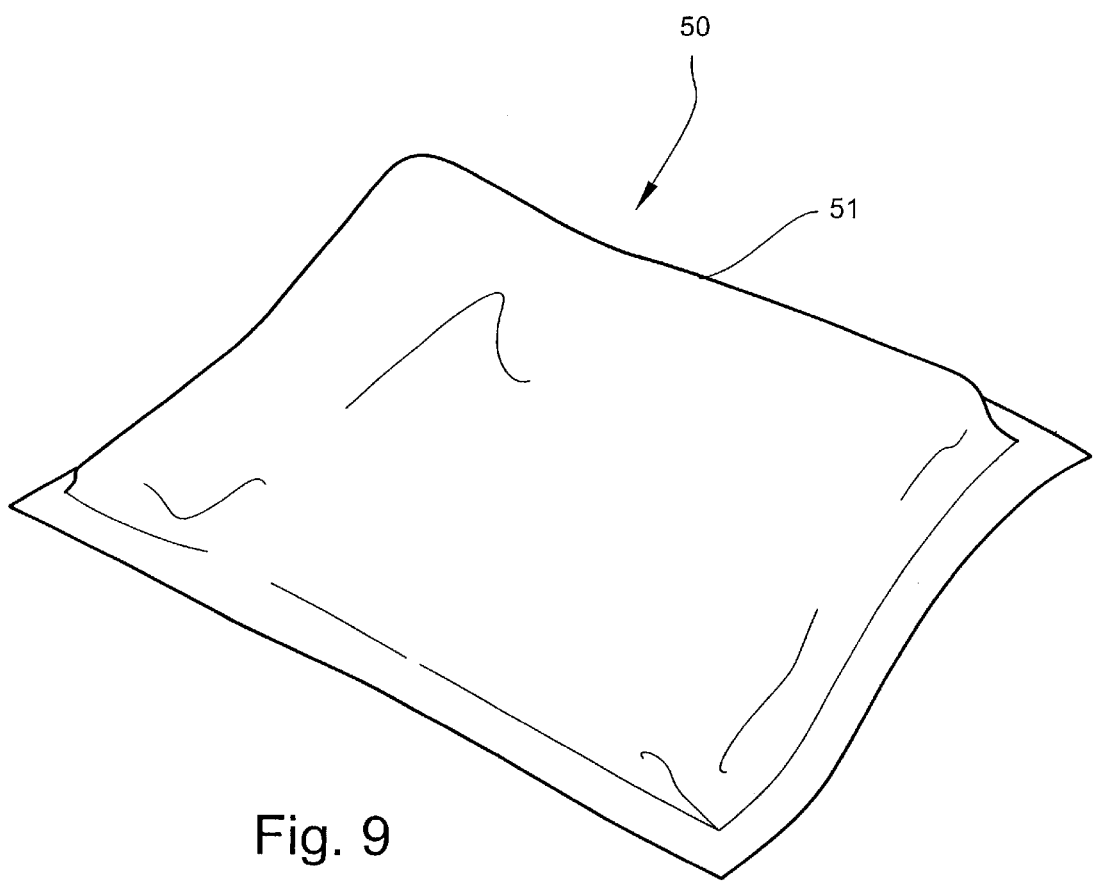
FIG. 9 is a perspective view of a wrist splint product according to a preferred embodiment of the invention.

Referring now to FIG. 9, a wrist splint product according to one preferred embodiment of the invention is illustrated and shown generally at reference numeral 50. The splint product 50 includes an outer moisture-impervious foil and laminated pouch 51. As is discussed in detail with reference to FIG. 10 below, the pouch 51 is the outermost protective enclosure within which wrist splints according to the present invention are sealed in the absence of moisture. The laminate structure of the outer pouch 51 may be formed from any suitable moisture-impervious materials; however, the pouch 51 is preferably formed from a 0.5 mil foil sheet sandwiched between two layers of low density polyethylene film. Each layer of polyethylene film has a thickness of 2.0 mils. The pouch 51 may optionally include an outer layer of laminated 60 gauge bi-axially oriented nylon film. When properly sealed, the laminate structure of the pouch 51 will prevent moisture intrusion indefinitely.

Figure 10:
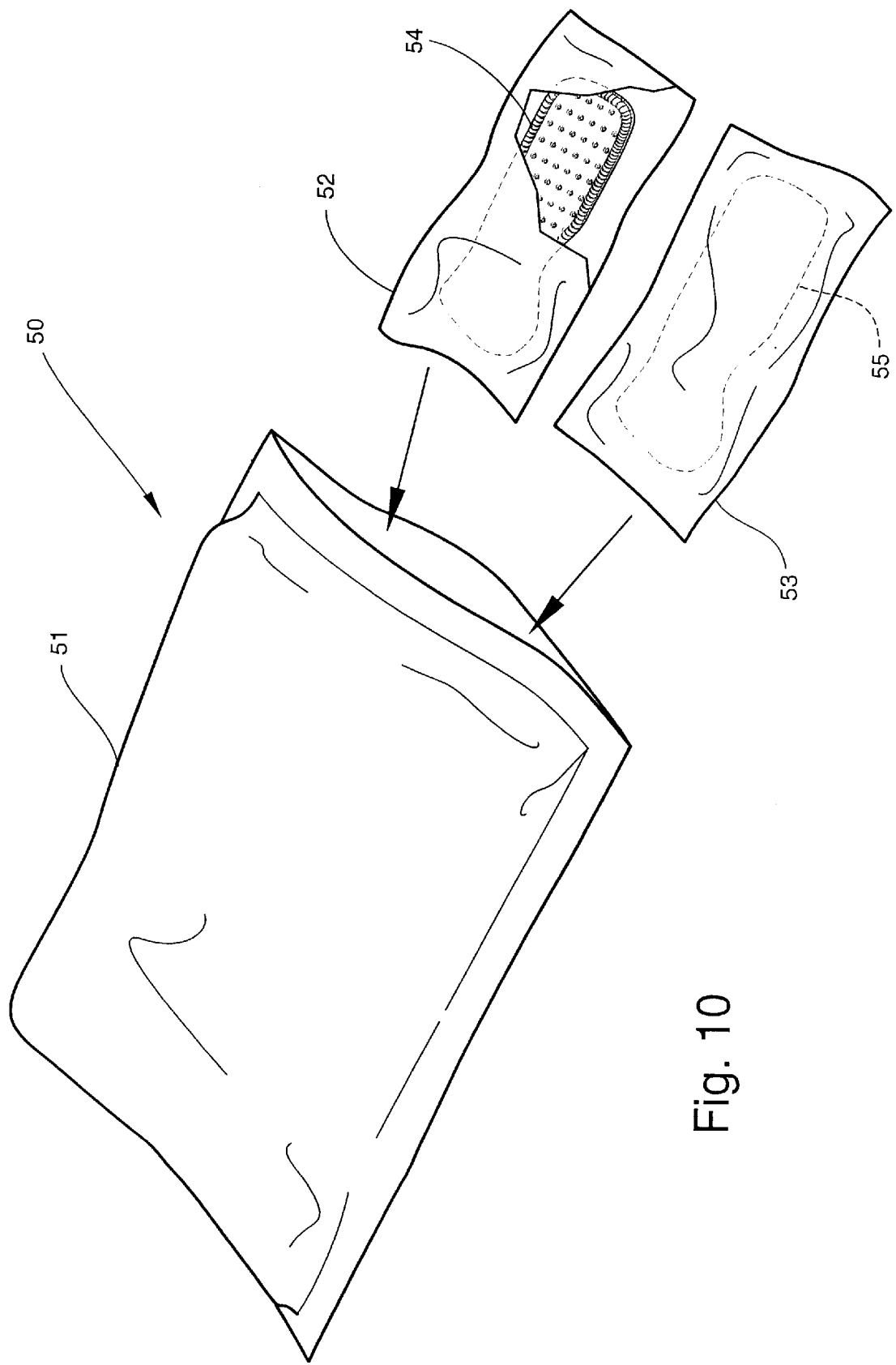
FIG. 10 is an exploded perspective view of a wrist splint product showing the outer moisture-proof packaging within which the splints are stored, and inner moisture-retardant packages within which the splints are also contained according to an alternative embodiment of the invention.

Referring now to FIG. 10, the contents of the outer pouch 51 are shown. The pouch 51 contains two inner, moisture-retardant pouches 52 and 53 in which respective splints 54 and 55 are sealed. The splints 54 and 55 are constructed from the same materials and include the same components as splints 11 and 12, respectively. Although they may be constructed from any suitable moisture-retardant materials, the inner pouches 52 and 53 are preferably constructed from 1.5 mil low density polyethylene. Low density polyethylene having thicknesses of up to 4.0 mils may also be used. The pouches 52 and 53 are sufficiently thin and porous that moisture will penetrate therethrough; however, such penetration is significantly retarded as compared to that which occurs as a result of direct exposure to atmospheric humidity so that any curing of the splints 54 and 55 that does occur happens at a greatly reduced rate.

The splints 54 and 55 are sealed within the moisture-free environment of the respective inner pouches 52 and 53 immediately prior to being sealed within the outer pouch 51. Sealing the inner pouches 14 and 15 in the pouch 11 in this manner gives the splints 54 and 55 an indefinite shelf life.

Figure 11:
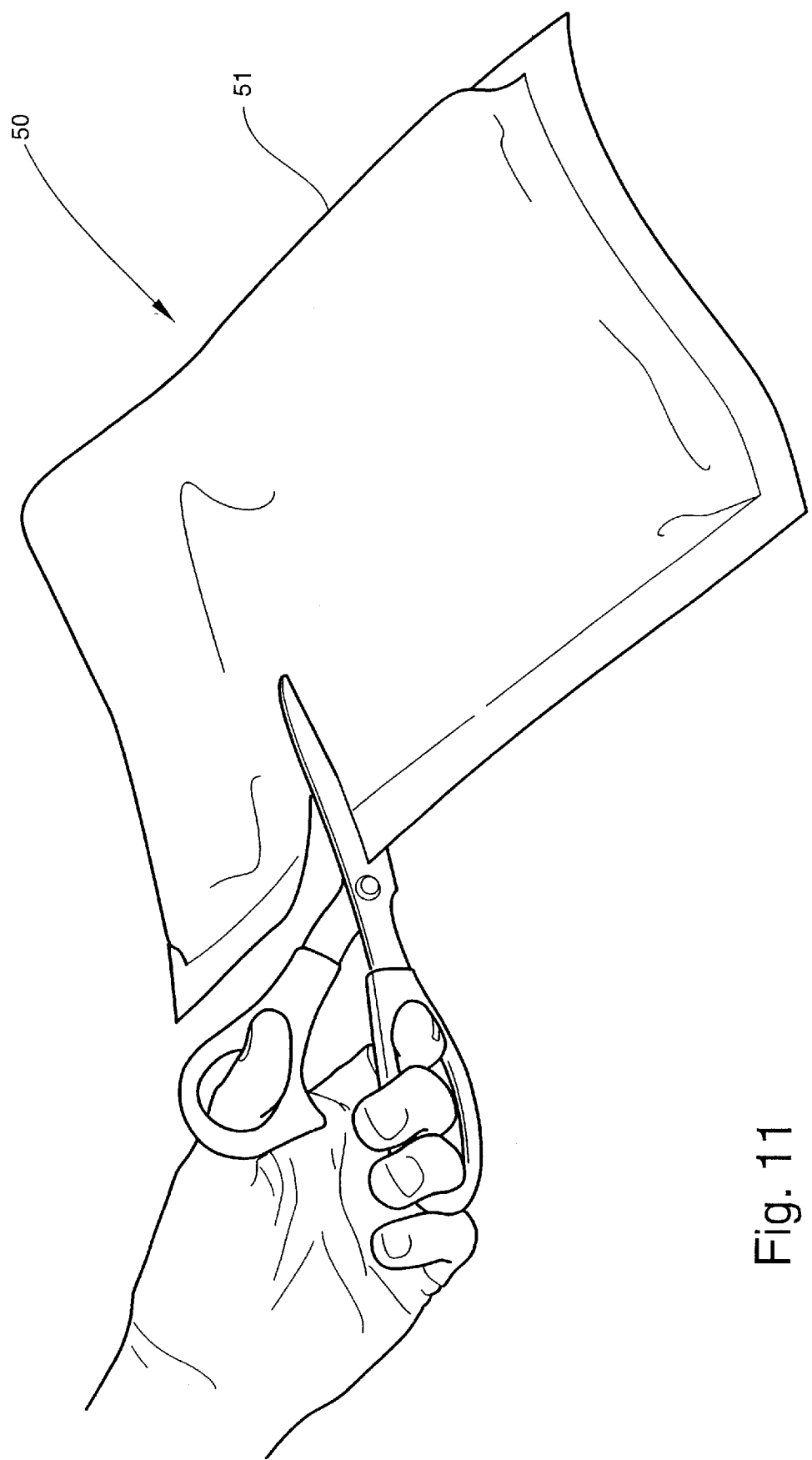
FIG. 11 is a perspective view illustrating a preferred method of opening the outer moisture-proof packaging.

Referring now to FIG. 11, when the splint product 50 is ready for use, the outer pouch 51 is cut open using scissors or a knife and the inner moisture retardant pouches 52 and 53 are removed. One of the pouches 52 or 53 is opened, and the other pouch 52 or 53 is left sealed. This greatly retards penetration of moisture into the unexposed splint 55 or 54 while the exposed splint 54 or 55, respectively, is being custom-molded to either the dorsal or volar aspect of a hand and wrist.

Figure 12:
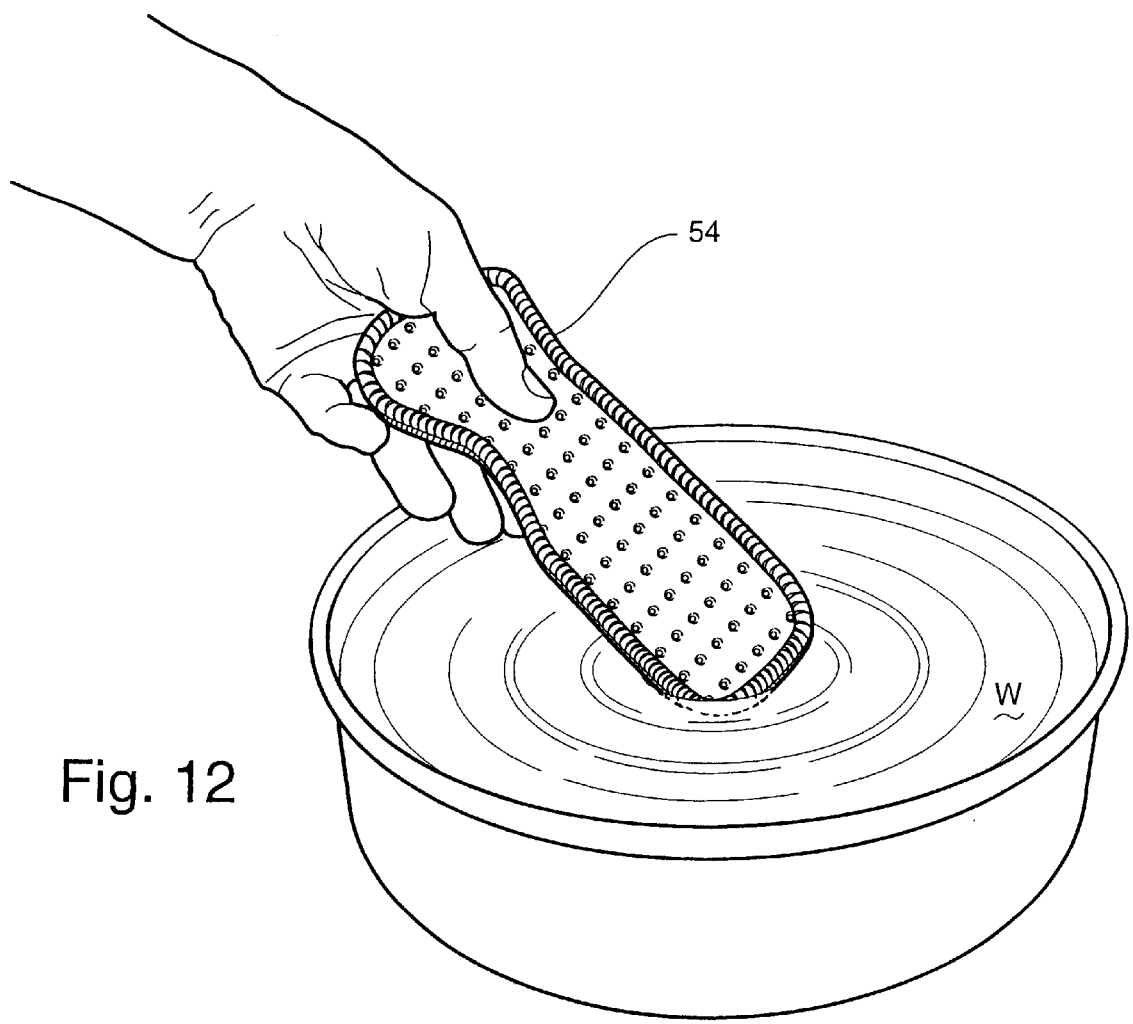
FIG. 12 is an environmental perspective view of a splint according to a preferred embodiment of the invention being immersed in water to initiate curing of the moisture-curable resin.

Referring now to FIG. 12 and using splint 54 as a representative example, the splint 54 is immersed in water "W" to activate the curing process. After it has been immersed, the splint 54 is removed from the water and excess moisture is squeezed from the splint 14, for example, by rolling the splint 54 in a towel (not shown). Alternatively, the splint 54 may be sprayed with water from a spray bottle, or allowed to harden gradually by exposure to atmospheric moisture. The wet splint 54 is then applied to either the dorsal or volar aspect of the hand and wrist to be supported. The pouch 53 is then opened, and this process is repeated with respect to splint 55.

Figure 13:
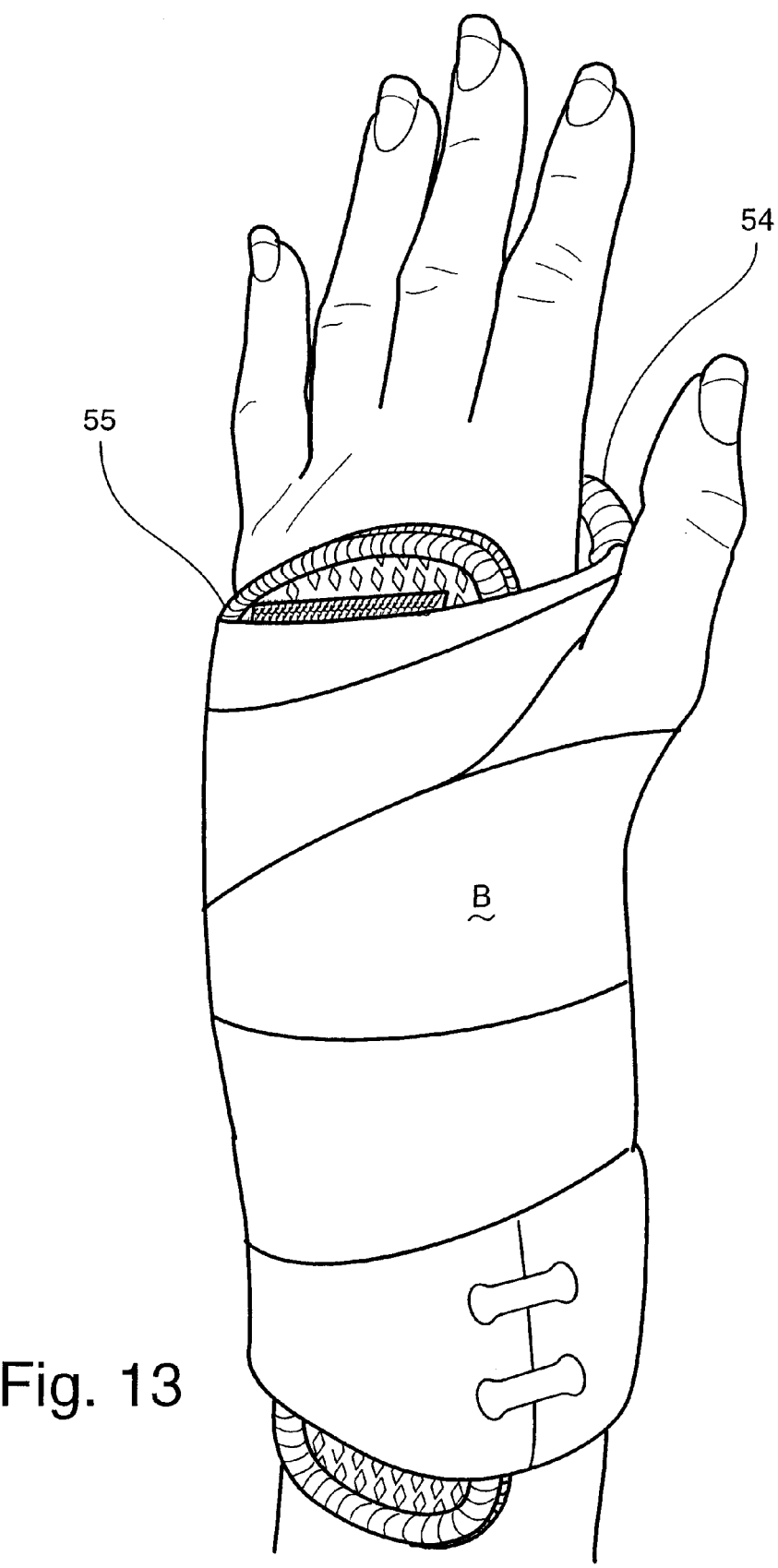
FIG. 13 is an environmental perspective view of splints secured to the left hand and wrist and overwrapped with an elastic bandage.

Referring now to FIG. 13, once the moistened splints 54 and 55 are in position against the respective volar and dorsal aspects of the hand and wrist, the hand and wrist are overwrapped with an elastic bandage "B". Although FIG. 13 shows the splints 54 and 55 positioned against the respective volar and dorsal aspects of the hand and wrist and over-wrapped by the elastic bandage "B" for simultaneous curing, the splints 54 and 55 may alternatively be custom-molded one at a time.

Figure 14:
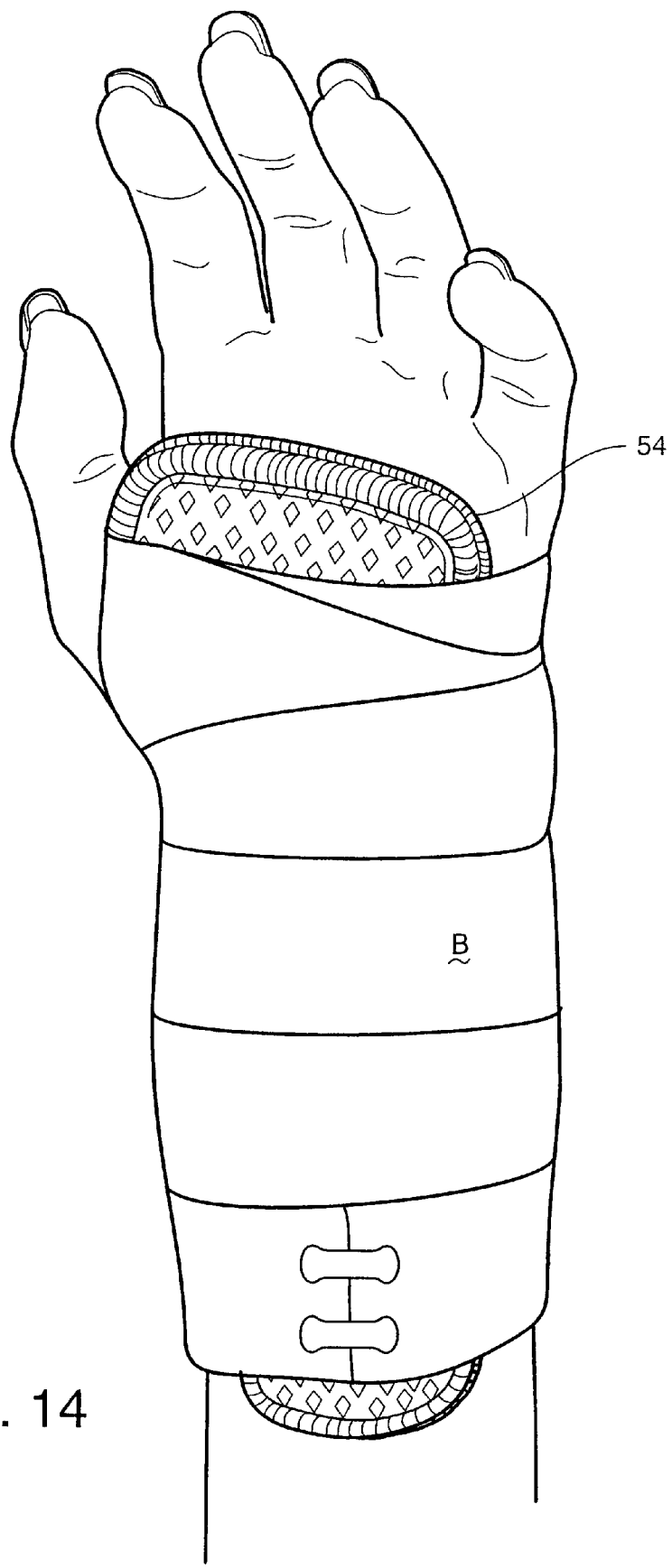
FIG. 14 is an environmental perspective view of a single splint secured to the left hand and wrist and overwrapped with an elastic bandage.

The splint 54 may be applied to either the volar aspect of the left hand or the dorsal aspect of the right hand. In contrast, splint 55 may be applied to either the volarl aspect of the right hand or the dorsal aspect of the left hand. Depending upon the severity of the injury and the degree of support desired, one or both of the splints 54 and 55 may be applied to the appropriate aspects of the affected hand. Preferably, both splints 54 and 55 are applied to the affected hand in the manner described above with reference to FIGS. 10 through 13. FIG. 14 shows the splint 54 being custom-molded to the volar aspect of the right hand and wrist. Regardless of the manner or order in which the splints 54 and 55 are cured, the patient must be advised not to attempt to flex or articulate the hand or wrist during the period of splint hardening.

Referring again to FIG. 13, the elastic bandage "B" remains wrapped in the position shown for at least a sufficient period of time for the splints 54 and 55 to completely harden into the proper conformation on the hand and wrist. The elastic bandage may be used continuously or intermittently, or the splints 54 and 55 may be worn after hardening without the elastic bandage "B".

A wrist splint assembly with custom-molded splints, a method of forming the custom-molded splints, and a wrist splint product are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A wrist splint assembly for being custom-fitted to a hand and wrist to be supported, comprising:
    (a) a first splint for being positioned against and formed to the volar aspect of the hand and wrist, and a second splint for being positioned against and formed to the dorsal aspect of the hand and wrist, each of said first and second splints defining a concave side edge extending inwardly toward the longitudinal axis of the splint for permitting ease of movement of the thumb and associated carpometacarpal joint of the hand against which the splint is positioned, and including:
        (i) an inner cushion layer for being placed on and conformed to the shape of the hand and wrist;
        (ii) an initially flexible intermediate layer overlying said inner cushion and comprising a substrate impregnated with a moisture-curable resin that hardens upon curing to form a rigid structure of the substrate that retains a shape into which it is molded during curing for maintaining the flexible inner cushion layer in a conforming shape against the hand and wrist;
        (iii) a flexible outer layer overlying the intermediate layer and attached to the inner cushion layer for enclosing the intermediate layer for forming the inner layer, intermediate layer and outer layer into a single, integrated splint structure; and
    (b) a support for retaining the first and second splints in position on the hand and wrist during use of said splint assembly.

2. A wrist splint assembly according to claim 1, wherein said support comprises an elongate strap having an outer surface and first and second ends, wherein said first end of the strap is releasably attached to a complementary fastener attached to a preselected one of the outer layers of the first and second splints, and said second end of the strap is releasably attached to said outer surface of the strap, thereby permitting the strap to encircle the wrist for securing the first and second splints against the hand and wrist.

3. A wrist splint assembly according to claim 2, wherein the support further comprises a second elongate strap having an outer surface and first and second ends, wherein said first end of said second strap is releasably attached to a complementary second fastener attached to a preselected one of the outer layers of the first and second splints, and said second end of the second strap is releasably attached to said outer surface of the second strap, thereby permitting the second strap to encircle the wrist for securing the first and second splints against the hand and wrist.

4. A wrist splint assembly according to claim 3, wherein the support further comprises a third elongate strap having an outer surface and first and second ends, wherein said first end of said third strap is releasably attached to a complementary third fastener attached to a preselected one of the outer layers of the first and second splints, and said second end of the third strap is releasably attached to said outer surface of the third strap, thereby permitting the third strap to encircle the hand for securing the first and second splints against the hand and wrist.

5. A wrist splint assembly according to claim 4, wherein said fastener, second fastener, and third fastener each comprise a patch of hooked material.

6. A wrist splint assembly according to claim 4, wherein the outer surface of the strap, second strap and third strap comprises looped material.

7. A wrist splint assembly according to claim 1, wherein said support comprises a plurality of elongate straps releasably attached to a plurality of complementary fasteners attached to the outer layer of the splint for permitting the straps to encircle and hold the splint in place against the wearer's hand and wrist while being worn.

8. A wrist splint assembly according to claim 7, wherein each of the straps comprises a patch of looped material attached to an end of the strap for cooperating with a complementary outer surface of the strap for holding the first and second splints in place against the hand and wrist while being worn.

9. A wrist splint assembly according to claim 1, and including a moisture-proof pouch in which the first and second splints are maintained in a flexible condition in a moisture-free environment until said pouch is opened immediately prior to applying one of the splints to the hand and wrist.

10. A wrist splint assembly according to claim 9, wherein said outer moisture-proof pouch is formed of a laminated structure having at least one layer of plastic film and at least one layer of aluminum foil bonded to the plastic film.

11. The wrist splint according to claim 1, wherein said substrate comprises a plurality of overlaid thicknesses of fiberglass fabric.

12. The wrist splint according to claim 11, wherein said plurality of thicknesses of fiberglass fabric comprises at least five thicknesses and no more than seven thicknesses.

13. A wrist splint product for being custom-fitted to a hand and wrist to be supported, comprising:
    (a) first and second splints, each of said first and second splints defining a concave side edge extending inwardly toward the longitudinal axis of said splint for permitting enhanced movement of the thumb and associated carpometacarpal joint of the hand, and each of said splints including a fabric impregnated with a moisture-curable resin that hardens upon curing to form a rigid structure of said fabric that retains a defined shape into which the fabric is molded during curing;
    (b) first and second inner storage pouches constructed of a plastic film having moisture-transmission retarding properties, one of said first or second splints being sealed in respective ones of the first and second storage pouches; and
    (c) a single, outer moisture-proof protective pouch within which the first and second splints and respective first and second inner storage pouches are sealed in the absence of moisture until the splint is to be molded to the body part to be protected.

14. The wrist splint product according to claim 13, wherein said outer moisture-proof protective pouch is formed of a laminated structure having at least one layer of plastic film and at least one layer of aluminum foil bonded to the plastic film.

15. The wrist splint product according to claim 14, wherein said plastic film has a thickness of 2 mils and said aluminum foil layer has a thickness of 0.5 mils, and wherein the at least one plastic film layer has a thickness of 2 mils and said aluminum foil layer has a thickness of 0.5 mils.

16. The wrist splint assembly according to claim 13, 14 or 15, wherein the outer moisture-proof protective pouch includes a laminated layer of nylon film.

17. A method of forming a custom-fitted wrist splint, comprising the steps of:

(a) providing a first splint for being positioned against and formed to the volar aspect of the hand and wrist, and a second splint for being positioned against and formed to the dorsal aspect of the hand and wrist, each of said first and second splints comprising a multi-layered protective pad positioned in flexible condition in a moisture-impervious storage package and sealed therein against entry of moisture until use and defining a concave side edge extending inwardly toward the longitudinal axis of the splint for permitting ease of movement of the thumb and associated carpometacarpal joint of the hand against which the splint is positioned, and including:

(i) an inner cushion layer for being placed on and conformed to the shape of the hand and wrist;

(ii) an initially flexible intermediate layer overlying said inner cushion and comprising a substrate impregnated with a moisture-curable resin that hardens upon curing to form a rigid structure of the substrate that retains a shape into which it is molded during curing for maintaining the flexible inner cushion layer in a conforming shape against the hand and wrist;

(iii) a flexible outer layer overlying the intermediate layer and attached to the inner cushion layer for enclosing the intermediate layer for forming the inner layer, intermediate layer and outer layer into a single, integrated splint structure;

wherein a support is carried by the first and second splints for retaining the first and second splints in position on the hand and wrist during use of said wrist splint;

(b) removing a preselected one of the first and second splints from said storage package;

(c) exposing the removed splint to moisture in an amount sufficient to activate the moisture-curable resin;

(d) placing the splint against the hand and wrist; and (e) exerting conforming pressure on the splint for a sufficient period of time for the pad to harden, whereby the pad hardens into a rigid, supporting shape custom-fitted to the hand and wrist.

* * * * *